United States Patent [19]

Burrows

[11] Patent Number: 5,435,909

[45] Date of Patent: Jul. 25, 1995

[54] WATER QUALITY MONITOR FOR A WATER PURIFICATION SYSTEM

[75] Inventor: Bruce D. Burrows, Valencia, Calif.

[73] Assignee: Hydrotechnology, Inc. a California corp., Valencia, Calif.

[21] Appl. No.: 212,364

[22] Filed: Mar. 14, 1994

[51] Int. Cl.⁶ .......................................... B01D 17/12
[52] U.S. Cl. ................................. 210/85; 210/87; 210/96.2; 210/121; 210/257.2; 324/439; 340/603
[58] Field of Search ...................... 210/85–87, 210/90, 91, 93, 94, 96.1, 96.2, 97, 98, 104, 110, 138, 257.1, 257.2, 259, 746, 121, 123, 128; 222/23, 64; 324/439, 443, 446; 340/603

[56] References Cited

U.S. PATENT DOCUMENTS

| | | | |
|---|---|---|---|
| 3,838,774 | 10/1974 | Dolan et al. | 210/85 |
| 3,990,066 | 11/1976 | Malmgren | 340/285 |
| 4,014,792 | 3/1977 | Gossett et al | 210/123 |
| 4,383,221 | 5/1983 | Morey et al. | 324/439 |
| 4,623,451 | 11/1986 | Oliver | 210/87 |
| 4,708,791 | 11/1987 | Dillard, III | 210/96.2 |
| 4,762,611 | 8/1988 | Schipper | 210/85 |
| 4,806,912 | 2/1989 | Clack | 340/603 |
| 4,849,098 | 7/1989 | Wilcock et al. | 210/85 |
| 4,851,818 | 7/1989 | Brown et al. | 340/603 |
| 4,937,557 | 6/1990 | Tucci et al. | 340/603 |
| 4,969,363 | 11/1990 | Mochizuki | 73/861.17 |
| 5,045,197 | 9/1991 | Burrows | 210/321.78 |
| 5,057,212 | 10/1991 | Burrows | 210/85 |
| 5,087,883 | 2/1992 | Hoffman | 324/443 |
| 5,096,574 | 3/1992 | Birdsong et al. | 210/90 |
| 5,145,575 | 9/1992 | Burrows | 210/85 |

FOREIGN PATENT DOCUMENTS 1111485 4/1989 Japan ......................... 210/86

*Primary Examiner*—Joseph W. Drodge
*Attorney, Agent, or Firm*—Kelly Bauersfeld & Lowry

[57] ABSTRACT

An improved water quality monitor is provided for use in a water purification system of the type having a reverse osmosis unit for producing relatively pure water from a tap water supply. The reverse osmosis unit supplies produced purified water to a reservoir for storage until dispensing, as by opening a faucet valve. An inlet shut-off valve closes to prevent tap water inflow to the reverse osmosis unit when the reservoir reaches a substantially filled condition. The water quality monitor includes electrodes in contact with the tap water and the produced purified water to obtain comparative conductivity readings which represent the performance level of the reverse osmosis unit in removing impurities from the tap water inflow. The monitor includes a test circuit responsive to movement of the inlet shut-off valve to take a conductivity reading at a point in time substantially after the shut-off valve opens to resume tap water inflow to the reverse osmosis unit, and substantially prior to shut-off valve closure when the reservoir reaches the filled condition. In one embodiment, the conductivity reading is triggered by the position of the inlet shut-off valve. In other embodiments, the conductivity reading is triggered in response to a float-mounted switch within the reservoir. In either case, the conductivity reading is stored in memory for subsequent periodic display, for example, each time the faucet valve is opened, by energization of one or more indicator lights.

21 Claims, 10 Drawing Sheets

WATER QUALITY MONITOR FOR A WATER PURIFICATION SYSTEM

BACKGROUND OF THE INVENTION

This invention relates generally to improvements in water purification systems of the type having a reverse osmosis unit or the like for removing dissolved ionic material and other contaminants from an ordinary supply of tap or feed water. More particularly, this invention relates to a reliable purity or water quality monitor for incorporation into a water purification system, wherein the monitor is responsive to cyclic operation of the reverse osmosis unit to accurately determine and indicate the operational efficiency of the reverse osmosis unit.

Water purification systems in general are well-known in the art of the type having a reverse osmosis unit for converting an incoming supply of ordinary tap or feed water into relatively purified water for use in cooking, drinking, etc. In general terms, the reverse osmosis unit includes a semi-permeable membrane through which a portion of the tap water supply is passed, such that the membrane acts essentially as a filter to remove dissolved metallic ions and the like as well as undesired particulate matter from the tap water. In operation, these impurities are removed from one portion of the water flow and concentrated in another portion of the flow which is normally discharged as waste to a drain. The thus-produced supply of relatively purified water is normally passed into a temporary storage reservoir or vessel where it is ready for dispensing and use, typically by operation of an appropriate faucet valve located adjacent a kitchen sink or the like. While the specific construction and operation of the purified water supply system may vary, such systems are exemplified by those shown and described in U.S. Pat. Nos. 4,585,554; 4,595,497; 4,657,674; and 5,045,197.

In many instances, it is desirable to obtain an indication of the degree of purity of the purified water produced by the reverse osmosis unit. Alternately stated, it is desirable to obtain an indication of the operating efficiency of the semi-permeable membrane within the reverse osmosis unit. In this regard, the level of water purity will depend upon and thus will vary in accordance with several factors, such as the cleanliness of the reverse osmosis unit membrane and the degree of contamination of the incoming tap water supply in a raw state. The purity level of produced purified water is normally indicated by a measurement of electrical conductivity, wherein a relatively high electrical conductivity correlates with a relatively low resistance and thus reflects a substantial quantity of remaining ionic material which has not been removed by the reverse osmosis unit. Conversely, a relatively low conductivity level indicates that a high proportion of ionic material as well as other contaminants have been removed. A failure of the purified water to meet certain purification criteria indicates that the water supply system may not be operating properly or otherwise that the semi-permeable membrane may need to be cleaned or changed.

In the past, test devices and systems have been proposed for use in measuring the conductivity level of the produced purified water in a typical purification system. In some cases, the conductivity of the produced purified water has been compared with the conductivity of the incoming tap water, thereby indicating the operational efficiency of the reverse osmosis unit in proportion to the condition of the tap water inflow. In general terms, such test devices and systems have utilized one or more electrodes for contacting the purified water and, in many designs, for contacting the incoming feed water, to obtain the desired water conductivity readings. These electrodes are coupled to an appropriate operating circuit and source of electrical power to obtain the desired purity level readings which can be indicated, for example, by illumination of one or more indicator lights.

Prior water quality monitor test devices have commonly comprised self-contained portable units intended for use by service personnel in testing purified water, as described, for example, in U.S. Pat. No. 3,990,066. More recently, reverse osmosis purification systems designed for under-the-counter use in a typical residence or office environment have been equipped with monitoring circuits integrated directly into the purification system, as shown, for example, in U.S. Pat. Nos. 4,623,451; 4,806,912; 3,838,774; 4,708,791; 5,057,212; and 5,145,575. Indicator lights in such test devices commonly include a red or yellow light energized when the quality of the produced purified water is unacceptable, and a green light energized when the conductivity reading or readings reflect acceptable water quality.

While these test devices beneficially provide important information regarding the performance of the reverse osmosis unit, cyclic operation of a typical reverse osmosis unit often results in erroneous test readings. More specifically, many reverse osmosis systems utilize an inlet shut-off valve which responds to the pressure of the produced purified water to turn off the tap water inflow when the storage reservoir reaches a substantially filled condition. The inlet shut-off valve beneficially stops water flow through the system when the reservoir is full, thereby preventing continuous wasted water flow to the drain. However, during the time that the inlet shut-off valve is closed, the pressure differential across the reverse osmosis membrane, necessary for production of purified water, is substantially removed. As a result, some migration or leaching of contaminants across the reverse osmosis membrane can occur, to increase the impurity level of small or isolated volumes of previously produced purified water resident within system flow paths between the membrane and the storage reservoir. Those flow paths provide a convenient mounting site for a pure water electrode, whereby a high and unacceptable conductivity reading can occur if a measurement is taken when the electrode is in contact with one of these isolated volumes of poor quality water. When system water flows resume upon dispensing of a sufficient portion of the purified water via a faucet valve or the like to re-open the inlet shut-off valve, any isolated volume or volumes of poor quality water mix quickly with other purified water so that the overall quality of the water actually dispensed is quite acceptable.

However, many conductivity test devices respond to faucet valve opening to immediately take a conductivity measurement, whereby the reading can be inaccurate if the inlet shut-off valve has been closed for an extended period of time. Other test devices operate by taking conductivity readings at set time intervals, whereby an inaccurate reading can occur if taken when the inlet shut-off valve is closed or shortly after opening thereof.

There exists, therefore, a significant need for further improvements in water quality monitors for testing and indicating the operating performance of a reverse osmosis unit in a water purification system, particularly wherein the water quality monitor is made responsive to cyclic operation of the reverse osmosis unit so that accurate and reliable test readings will result. The present invention fulfills these needs and provides further related advantages.

SUMMARY OF THE INVENTION

In accordance with the invention, an improved water quality monitor is provided for use in a water purification system of the type having a reverse osmosis unit for producing relatively purified water from an incoming tap water supply. The purification system includes a storage reservoir for receiving and storing the produced purified water for immediate dispensing via a faucet valve or the like. A tap water inlet shut-off valve responds to the water level within the storage reservoir to shut off tap water flow to the reverse osmosis unit when the reservoir reaches a substantially filled condition. The water quality monitor includes a test circuit to determine the purity level of the produced purified water in response to cyclic operation of the reverse osmosis unit, as reflected in the preferred embodiment by opening and closure movement of the shut-off valve, or in other preferred embodiments by response to the water level within the reservoir. In either case, the test circuit is designed to take water conductivity readings of the tap water and produced purified water at a point in time which is substantially mid-cycle, namely, substantially after the shut-off valve moves to an open position and substantially prior to return movement of the shut-off valve to the closed position when the reservoir is filled. During this so-called mid-cycle condition, the reverse osmosis unit produces purified water with a substantially optimum efficiency, so that accurate conductivity test readings reflective of the actual quality of the purified water can be taken. The conductivity readings are stored in a memory for subsequent display, for example, when a faucet valve or he like is opened to dispense water.

In accordance with one preferred form of the invention, the inlet shut-off valve includes a diaphragm-mounted valve member defining differential areas on opposite sides thereof for comparative response to the pressure of the tap water supply and to the pressure of the produced purified water within the storage reservoir. As the storage reservoir approaches a substantially filled condition, the pressure level of the produced purified water increases. When the pressure level of the produced purified water reaches a point reflective of a substantially filled reservoir condition, the shut-off valve moves to the closed position, thereby disconnecting the tap water supply from the reverse osmosis unit to turn the system off. Subsequent dispensing of a sufficient quantity water from the storage reservoir causes the pressure level of the produced purified water to drop sufficiently so that the inlet shut-off valve moves to the open position. As a result, tap water inflow to the reverse osmosis unit is resumed, to correspondingly resume pure water production. A water purification system of this general type is described in detail in U.S. Pat. No. 5,045,197, which is incorporated by reference herein. Importantly, during the off condition, the normally existent pressure differential across the reverse osmosis unit is removed, such that some migration of previously removed contaminants can leach or migrate to the previously produced purified water.

The present invention recognizes that migration of contaminants to the produced purified water, during a system off cycle, can result in localized water volumes having unacceptably high conductivity levels. While these localized water volumes tend to intermix with other purified water so that the water actually dispensed is of acceptable quality, inaccurate conductivity readings may nevertheless occur as these localized water volumes pass conductivity electrodes of the water quality monitor.

Accordingly, in the present invention, conductivity readings reflecting water quality of the produced purified water are taken at a point in time substantially after movement of the shut-off valve to the open position, such that localized volumes of unacceptable quality water are permitted to move past the monitoring electrodes before a test reading is taken. Similarly, the present invention insures that test readings are taken substantially prior to reclosure of the shut-off valve. In this manner, conductivity readings are confined to a point in time when the reverse osmosis unit is operating at substantially full pressure differential conditions, and after any localized or isolated volumes of poor quality water have flushed past a pure water electrode. As a result, the conductivity readings will accurately reflect actual operating efficiency of the reverse osmosis unit.

The test circuit of the present invention, in accordance with a preferred embodiment, is armed by a reset switch each time the inlet shut-off valve moves from the closed position to the open position to permit resumed system flows and pure water production. In the preferred form, this occurs by movement of a reed switch or the like responsive to opening displacement of the inlet shut-off valve. Return movement of the shut-off valve toward the closed position, which occurs relatively slowly as the reservoir fills, is effective to trigger the test circuit to produce a test pulse utilized to obtain comparative conductivity readings of the tap water and purified water supplies. This test pulse is delivered at a point in time which is substantially mid-cycle between opening movement and subsequent closure of the inlet shut-off valve. The test result is stored in memory for subsequent display, in the preferred form, each time a faucet valve is opened to dispense water.

In one alternative preferred embodiment, the reset switch is provided as part of a float unit mounted within the storage reservoir. The reset switch responds to a fall in the reservoir water level, indicative of water dispensing and opening of the inlet shut-off valve to resume tap water inflow, to open the test circuit. A subsequent rise in reservoir water level, reflective of a mid-cycle condition, is effective to trigger the test pulse used for taking the conductivity reading. This float-mounted reset switch may be used in combination with the pressure responsive shut-off valve as previously described. Alternately, additional float-mounted switches may be provided within the reservoir to provide appropriate signals to a solenoid-type valve actuator used to move the inlet shut-off valve between the open and closed positions.

In accordance with other aspects of the invention, the purification system includes a prefilter stage disposed upstream from the reverse osmosis unit for removing particulate from the tap water inflow, wherein such particulate could otherwise cause premature clogging and failure of a reverse osmosis membrane. The test circuit includes a pressure sensor for detecting the pressure drop across the prefilter stage, and for indicating when that pressure drop reaches a level such that a removable prefilter cartridge should be changed.

The test circuit further includes means for indicating system failure reflected by the shut-off valve remaining in an open condition for an excessive period of time. A battery power supply is conveniently provided for the test circuit, and means are also provided for indicating low battery power.

According to another feature of the invention, a novel flow switch is provided to detect dispensing of purified water by opening of a faucet valve or the like. The improved flow switch includes means for tracking the volume of water dispensed so that a postfilter cartridge can be changed when a predetermined volume of water is dispensed from the system.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
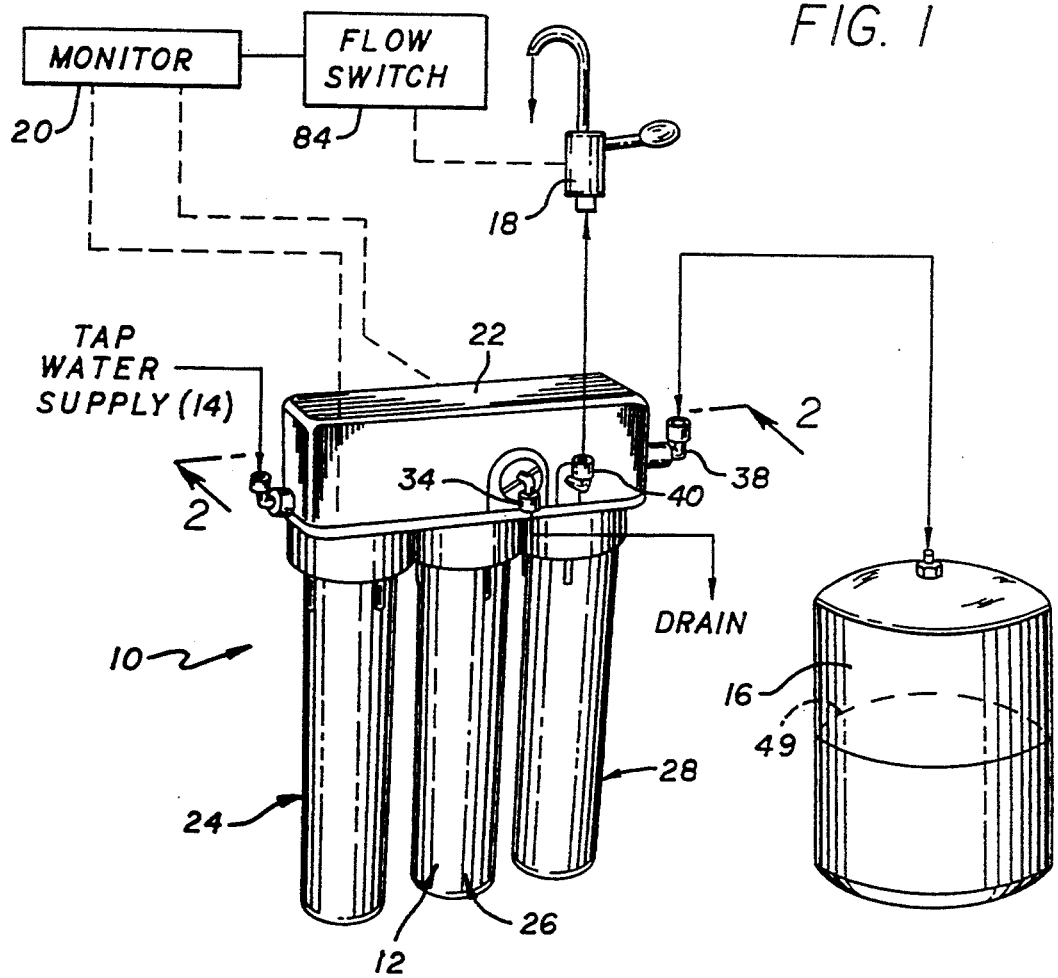
FIG. 1 is a front perspective view, partially in schematic form, illustrating a water purification system and related water quality monitor embodying the novel features of the invention.

As shown in the exemplary drawings, a water purification system referred to generally in FIG. 1 by the reference numeral 10 includes a reverse osmosis unit 12 for producing relatively purified water from an ordinary tap water supply 14 or the like. The produced purified water is collected within a suitable storage reservoir 16 and/or dispensed on demand, as by means of a faucet valve 18 or the like. A water quality monitor referred to generally by reference numeral 20 is provided for testing the purity level of produced purified water, and for indicating the purity level as by illumination of appropriate indicator lights (not shown in FIG. 1). The water quality monitor 20 is adapted to operate in response to normal cyclic operation of the reverse osmosis unit 12, to provide accurate and reliable test readings indicating system performance.

The water purification system 10 is designed particularly for use in residential and other domestic applications to provide a readily available supply of purified water. As is known in the art, the purification system 10 utilizes principles of reverse osmosis to convert the tap water inflow 14 into a pair of water outflows respectively comprising the relatively purified water having contaminants removed therefrom, and a waste or reject water supply having contaminants and/or impurities concentrated therein. The produced purified water is normally coupled to the storage reservoir 16 for collection and storage, and also to the faucet valve 18 for dispensing on demand for drinking, cooking, etc. One or more parallel-connected dispense paths to a refrigerator ice maker (not shown) and the like may also be provided. The reject water supply, often referred to as brine is normally discharged to a suitable drain.

Figure 2:
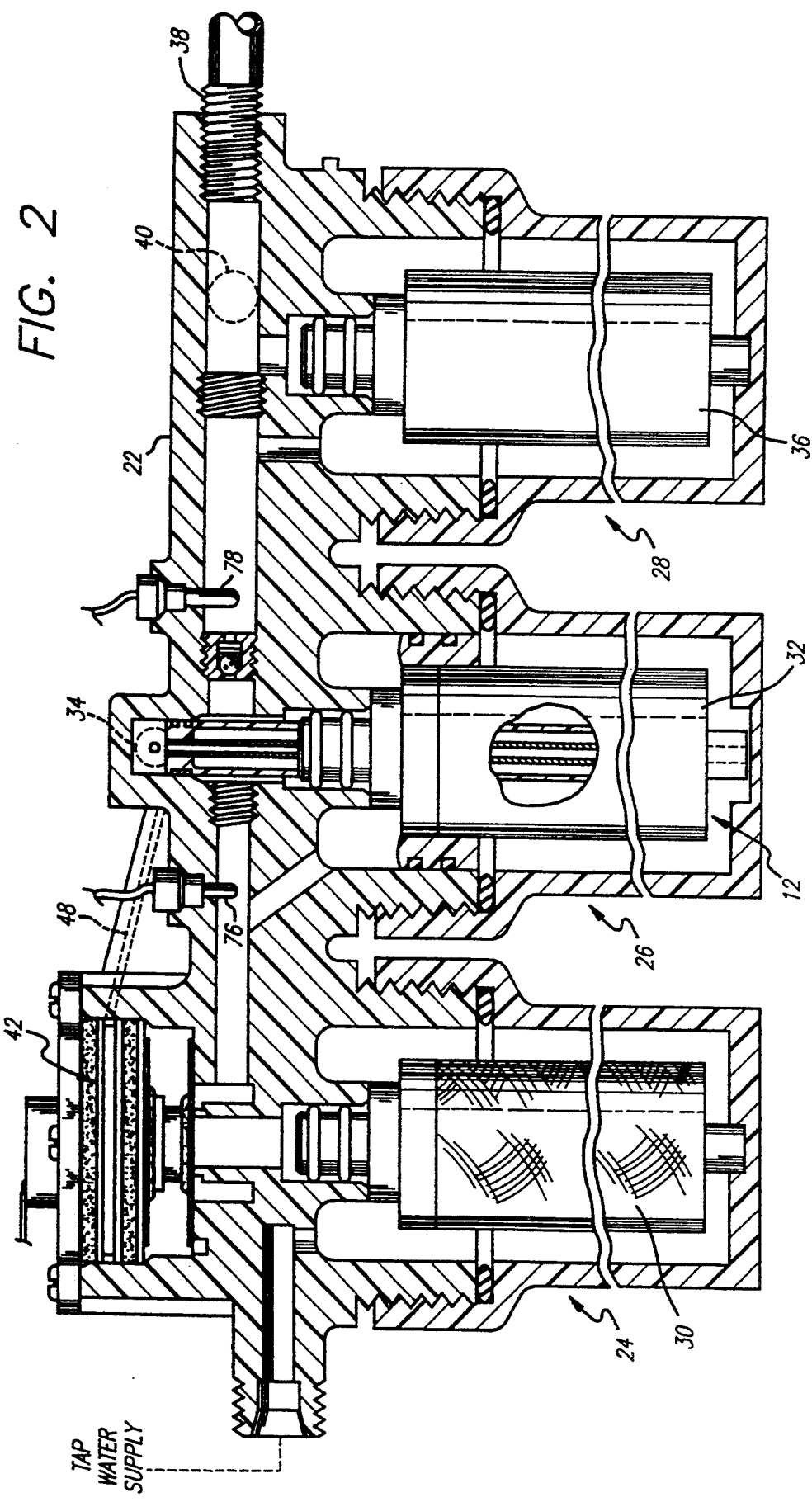
FIG. 2 is an enlarged fragmented vertical sectional view taken generally on the line 2—2 of FIG. 1.

FIGS. 1 and 2 show the purification system 10 in a preferred configuration, in conformance with the water purification system disclosed in U.S. Pat. No. 5,045,197, which is incorporated by reference herein. As shown, the purification system 10 comprises a unitized manifold 22 which supports three processor stages 24, 26, and 28 for converting the tap water inflow 14 into the separated purified and reject water supplies, as described above. In this regard, the first stage 24 comprises an initial filtration or prefilter stage for flow-through passage of the tap water inflow 14 through a prefilter cartridge 30 (FIG. 2) to remove particulate therefrom. The resultant prefiltered tap water passes to the second stage 26, which comprises the reverse osmosis unit 12 and includes a reverse osmosis semipermeable membrane 32 (FIG. 2). In the presence of appropriate pressure conditions as known in the art, the membrane 32 functions to separate the tap water inflow 14 into the purified and reject water supplies. The reject water supply is connected through a suitable drain fitting 34 (FIG. 1) for passage to the drain, whereas the produced purified water is connected to the third or final stage 28 comprising a postfilter stage. The purified water flows through a postfilter cartridge 36 and further through a tank fitting 38 for collection and storage within the reservoir 16, or through a dispense fitting 40 for delivery and dispensing via the faucet valve 18 or the like.

An inlet shut-off valve 42 is carried by the manifold 22 and responds to the level of produced purified water within the reservoir 16 to cycle the system between an "on" state and an "off" state. More particularly, as shown best in FIGS. 2-4, the inlet shut-off valve 42 comprises a valve member 44 of differential area mounted on a resilient diaphragm for opening and closing movement to respectively permit and prevent tap water inflow to the reverse osmosis unit 12. In one preferred form, a lower and relatively small area face of the valve member 44 is subjected to the pressure of the tap water supply by direct communication with a discharge port 46 associated with a downstream side of the prefilter stage 24. An upper and comparatively larger surface area of the valve member 44 is exposed to the pressure of produced purified water within a pressure chamber 47 connected via a pressure port 48 to produced purified water discharged from the reverse osmosis unit 12. Accordingly, the pressure within the chamber 47 corresponds to the pressure of purified water within the reservoir 16. The valve member 44 responds to the pressure differential applied thereto, for shutting off tap water inflow when the reservoir 16 reaches a substantially filled condition. By contrast, the valve member responds to this same pressure differential to open and permit resumed tap water inflow when a sufficient quantity of the purified water is dispensed, as by opening the faucet valve 18, to reduce the pressure within the reservoir 16.

More particularly, during normal operation of the reverse osmosis unit 12 to produce purified water, with the inlet shut-off valve 42 in a full open position (FIG. 3), the membrane 32 of the reverse osmosis unit 12 is subjected to a substantial pressure differential enabling production of purified water. The produced purified water is coupled for flow into the reservoir 16, wherein the reservoir commonly includes an internal resilient bladder 49 (FIG. 1) which subdivides the reservoir interior into a gas-filled pressure chamber and a water chamber for receiving and storing the purified water. As the reservoir 16 approaches a substantially filled condition, the bladder 49 deforms to reduce the volume of the pressure chamber and thereby result in a progressively increased pressure applied to the purified water. As the pressure applied to the purified water increases, the pressure differential across the reverse osmosis unit 12 gradually decreases. The operating efficiency of the reverse osmosis membrane 32 is in part dependent upon the magnitude of the pressure differential applied thereto. This same pressure differential is applied as described above across the valve member 44.

To ensure satisfactory system performance in the production of purified water, the shut-off valve 42 is designed to close when this pressure differential across the membrane 32 reaches a predetermined but still substantial minimum level. For example, in a system subjected to a tap water supply pressure of about 60 psi, the valve member 44 of the shut-off valve 42 is designed with appropriate differential upper and lower surface areas to close when the pressure of the produced purified water reaches a predetermined threshold of about 40 psi. This closure operation is achieved by exposing the larger upper surface area of the valve member 44 to the pressure of produced purified water, in contrast with the proportionately smaller lower surface area of the valve member exposed through the port 46 to the tap water supply pressure.

Figure 3:
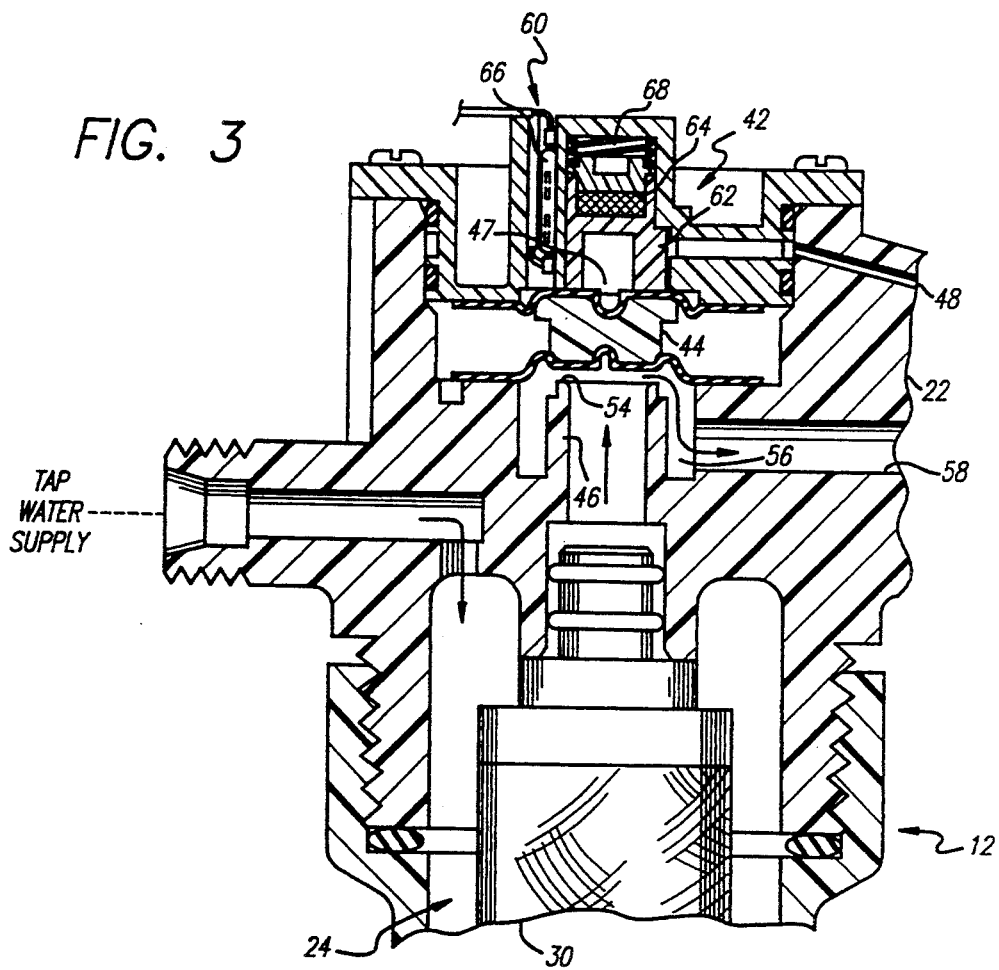
FIG. 3 is an enlarged fragmented vertical sectional view corresponding generally with a portion of FIG. 2, and showing an inlet shut-off valve in a fully open position.

With this geometry, when the pressure of the purified water falls below the level indicative of a substantially filled reservoir 16, the pressure differential across the valve member 44 is sufficient to displace the valve member to an open condition (FIG. 3). The shut-off valve 42 is conveniently designed for snap-action movement to a substantially full-open position by providing an annular valve seat 54 engaged by the lower side of the valve member 44 in the closed position, wherein the valve seat 54 is surrounded by an annular gallery 56 coupled to a flow passage 58 leading to the reverse osmosis unit 12. With this construction, as soon as the valve member 44 moves to a slightly opened state, the cross sectional area exposed to the tap water pressure increases significantly, resulting in effective snap-action movement to the full open position. Supply of the tap water 14 to the reverse osmosis unit 12 is thus resumed to correspondingly resume production of purified water. Moreover, this shut-off valve construction assures that a substantial quantity of the purified water will be dispensed from the full reservoir before the shut-off valve will open, thereby also assuring that the system will thereafter operate for a substantial period of time to produce purified water to re-fill the reservoir. For example, in the illustrative embodiment, the flow area of the port 46 in combination with the gallery 56 provide dispensing of about one gallon from a full three gallon reservoir before the inlet shut off valve opens.

As the reservoir 16 approaches a filled condition, the pressure differential across the valve member 44 decreases at a slow rate since purified water production proceeds at a relatively slow flow rate. Eventually, the pressure differential across the valve member 44 approaches a condition causing the valve member 44 to displace slowly toward the closed position. As this pressure differential decreases, and the valve member 44 moves slowly to the closed position, it is known that the operating efficiency of the reverse osmosis membrane 32 also decreases.

The water quality monitor 20 of the present invention responds to the above-discussed cyclic operation of the purification system to take water quality test readings within a restricted portion of the system operation cycle when the reverse osmosis unit 12 is substantially at maximum operating efficiency. That is, the present invention recognizes that closure of the inlet shut-off valve 42 removes the pressure differential across the reverse osmosis membrane 32, such that some of the previously-removed contaminants and impurities can leach or migrate across the membrane to contaminate localized portions of the previously produced purified water within pure water flow paths of the system manifold 22. The improved water quality monitor of the present invention thus does not take test readings within a period of time that the inlet shut-off valve is closed, or immediately after opening thereof, to avoid inadvertent and inaccurate reading of a localized pocket of poor quality water. Similarly, the present invention does not take a test reading during the period of time that the shut-off is near the closed condition, since the reduced pressure differential causes the reverse osmosis unit to function at less than maximum operating efficiency. Instead, all test readings are taken during system operation with a substantially optimum pressure differential across the reverse osmosis unit, referred to herein as mid-cycle. The test readings are stored in memory for subsequent and periodic display, for example, each time the faucet valve 18 is opened to dispense water.

Figure 4:
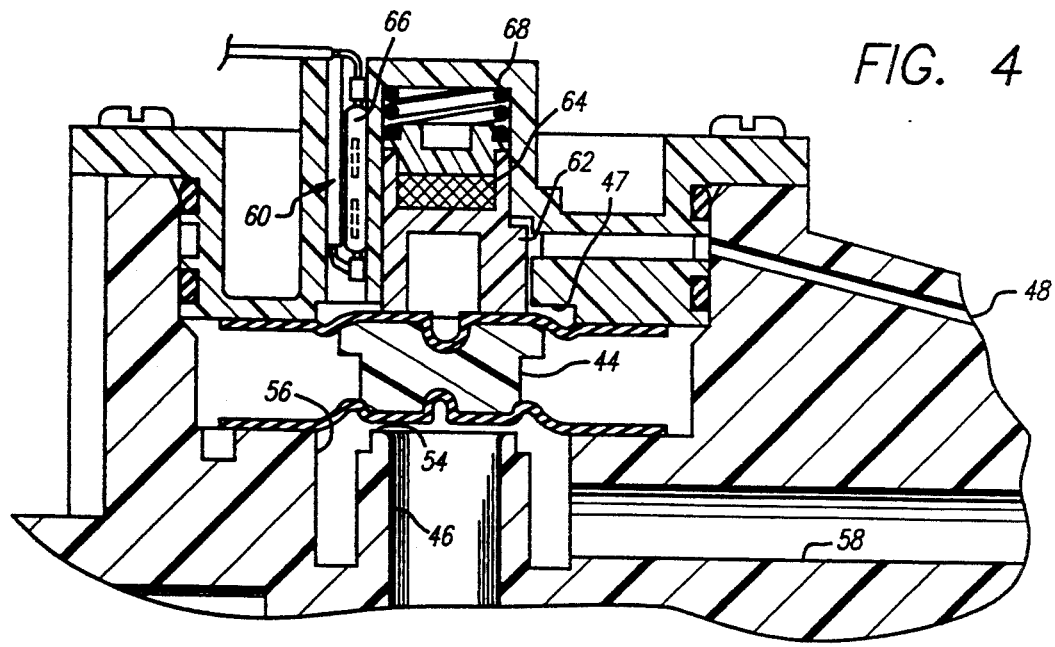
FIG. 4 is an enlarged fragmented vertical sectional view generally similarly to FIG. 3, and illustrating the inlet shut-off valve in a partially closed position.

Operation of the water quality monitor 20, in coordination with cyclic operation of the reverse osmosis unit 12, is obtained by means of a reset switch 60 associated with the inlet shut-off valve 42. As shown in FIGS. 2-4, in accordance with the preferred form of the invention, a shuttle piston 62 carries a magnet 64 in close association with a reed switch 66 mounted above the shut-off valve. A low force spring 68 may be provided to ensure piloted back-and-forth movement of the shuttle piston 62 and magnet thereon with the diaphragm-mounted valve member 44. The reed switch 66 is positioned to be closed each time the valve member 44 moves to the full open position. As the valve member 44 transitions slowly toward the closed position, passing a point about half-way to a fully closed state, the magnet 64 switches the reed switch 66 to an open state. This opening and closure movement of the reed switch 66 is effective to operate the water quality monitor 20, as will be described in more detail. Although the reed switch 66 is moved to the open state when the shut-off valve member 44 is about half-way toward the closed position, it will be understood that this may and will often occur at a point in time which is more than half-way between valve member opening and subsequent closure.

Figure 5:
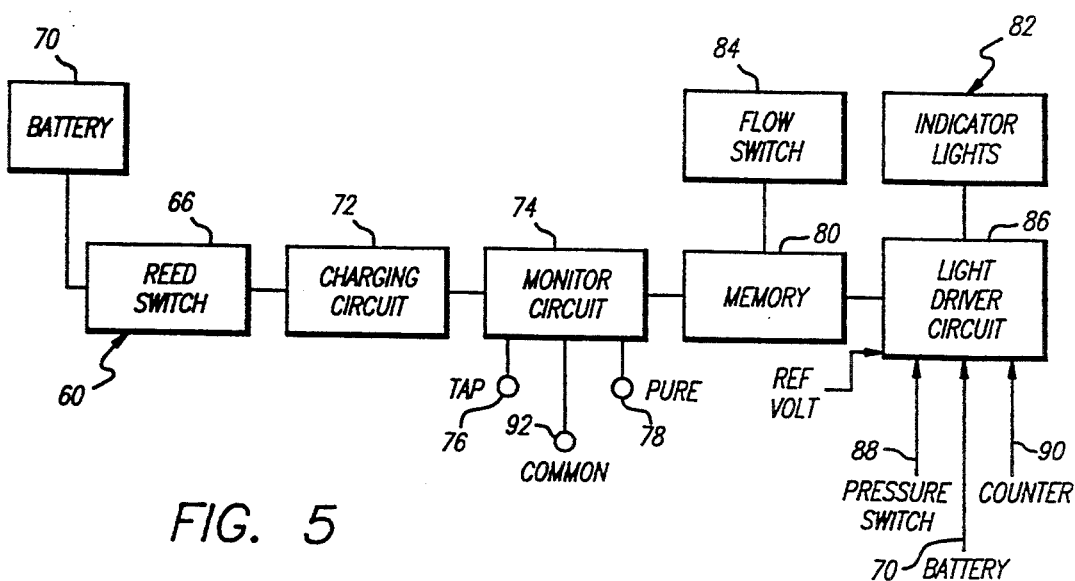
FIG. 5 is a circuit block diagram illustrating the water quality monitor for use in the purification system of FIGS. 1-4.

FIG. 5 is a schematic block diagram illustrating the structure and functional operation of the water quality monitor. In particular, the reset switch 60 is connected to a convenient and appropriate power source, such as a 9-volt battery 70. When the reed switch 66 is closed upon movement of the shut-off valve 42 to the full open position to resume tap water inflow to the purification system, a charging circuit 72 is connected to the battery 70. The charging circuit 72 functions to develop an appropriate electrical charge which is stored until the reed switch 66 opens. As described above, opening movement of the reed switch 66 occurs in response to movement of the shut-off valve member 44 to a position reflective of a mid-cycle condition of the reverse osmosis unit 12, wherein the system is operating substantially at full pressure to produce purified water. When the reed switch opens, the charging circuit delivers a pulse to a monitor circuit 74 to couple an appropriate test pulse to a tap water electrode 76 and to a pure water electrode 78. These electrodes are conveniently mounted at appropriate positions along flow paths within the manifold 22, as shown in FIG. 2. The monitoring circuit 74 functions to determine the comparative conductivities of the tap water inflow 14 and produced purified water, for purposes of monitoring the operating efficiency of the reverse osmosis unit 12.

As shown in FIG. 5, the test reading taken by the monitor circuit 74 is delivered to a memory 80 for storage and subsequent display. Conveniently, the monitoring circuit 74 may take any one of several forms known in the art, particularly such as those monitoring circuits described in U.S. Pat. Nos. 5,057,212 and 5,145,575 which are incorporated by reference herein. The test reading stored in memory 80 is subsequently and periodically displayed by means of an appropriate signal such as indicator lights 82. In accordance with a preferred form of the invention, the display is triggered each time pure water is dispensed such as when the faucet valve 18 is opened, which correspondingly causes a flow switch 84 or the like to trigger the memory 80 for purposes of displaying the stored test reading via energization of the appropriate indicator light 82. As one example, a green indicator light can be illuminated when the conductivity test reading stored in memory indicates acceptable quality of the purified water. By contrast, a yellow indicator light can be illuminated when the test reading indicates unacceptable water quality. When the water quality is unacceptable, proper system performance is typically restored by changing the reverse osmosis membrane 32.

The water quality monitor 20 is also designed, in preferred form, to operate the indicator lights 82 in a manner signalling other system conditions for which remedial action may be desirable or necessary. Specifically, the bank of indicator lights 82 is operated by a light driver circuit 86 adapted to receive auxiliary inputs reflective of important system conditions. As shown in FIG. 5, one auxiliary input is obtained from a pressure sensor or switch 88 which indicates the tap water pressure at the downstream side of the prefilter stage 24. When that pressure falls to a predetermined level indicative of a substantially clogged prefilter cartridge 30 (FIG. 2), the light driver circuit 86 responds to operate the indicator lights 82 in a known manner, for example, by illuminating all of the lights simultaneously.

The light drive circuit 86 also receives an input from the battery 70. When the detected battery voltage falls below a threshold level, indicating that the battery 70 needs to be replaced, the driver circuit 86 responds to control the indicator lights in a manner reflecting low battery power, such as by preventing illumination of any light when a test reading should normally be displayed.

Another input to the light driver circuit 86 is obtained from a counter 90 which counts the number of times that the flow switch 84 is operated by opening the faucet valve 18, without closure of the inlet shut-off valve 12. In this regard, long-term operation of the purification system 10 without periodic closure of the shut-off valve 42 normally indicates a mechanical failure of the shut-off valve 42. The counter 90 thus signals the light driver circuit 86 when this condition occurs so that the indicator lights will be operated in a known manner, such as by illumination of a red indicator light.

FIGS. 6A–6D show the water quality monitor 20 in a preferred circuit implementation in accordance with the functional operating features described above. It will be understood by persons skilled in the art, however, that these functional features can be carried out in a variety of different circuit arrangements.

Figures 6, 6A:
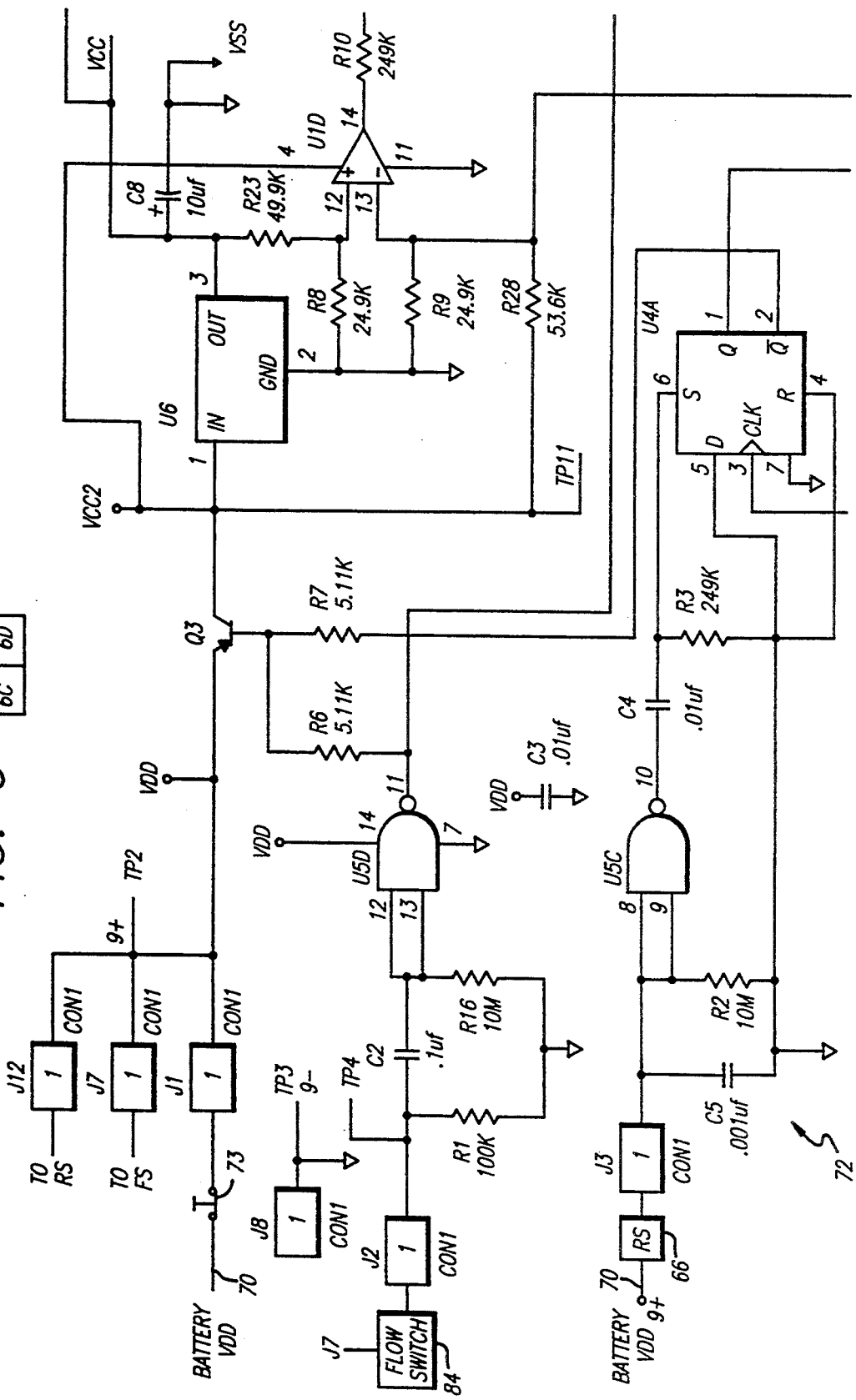
FIG. 6, encompassing
FIGS. 6A-6D, is a detailed circuit diagram depicting one preferred form of the invention.
Figure 6B:
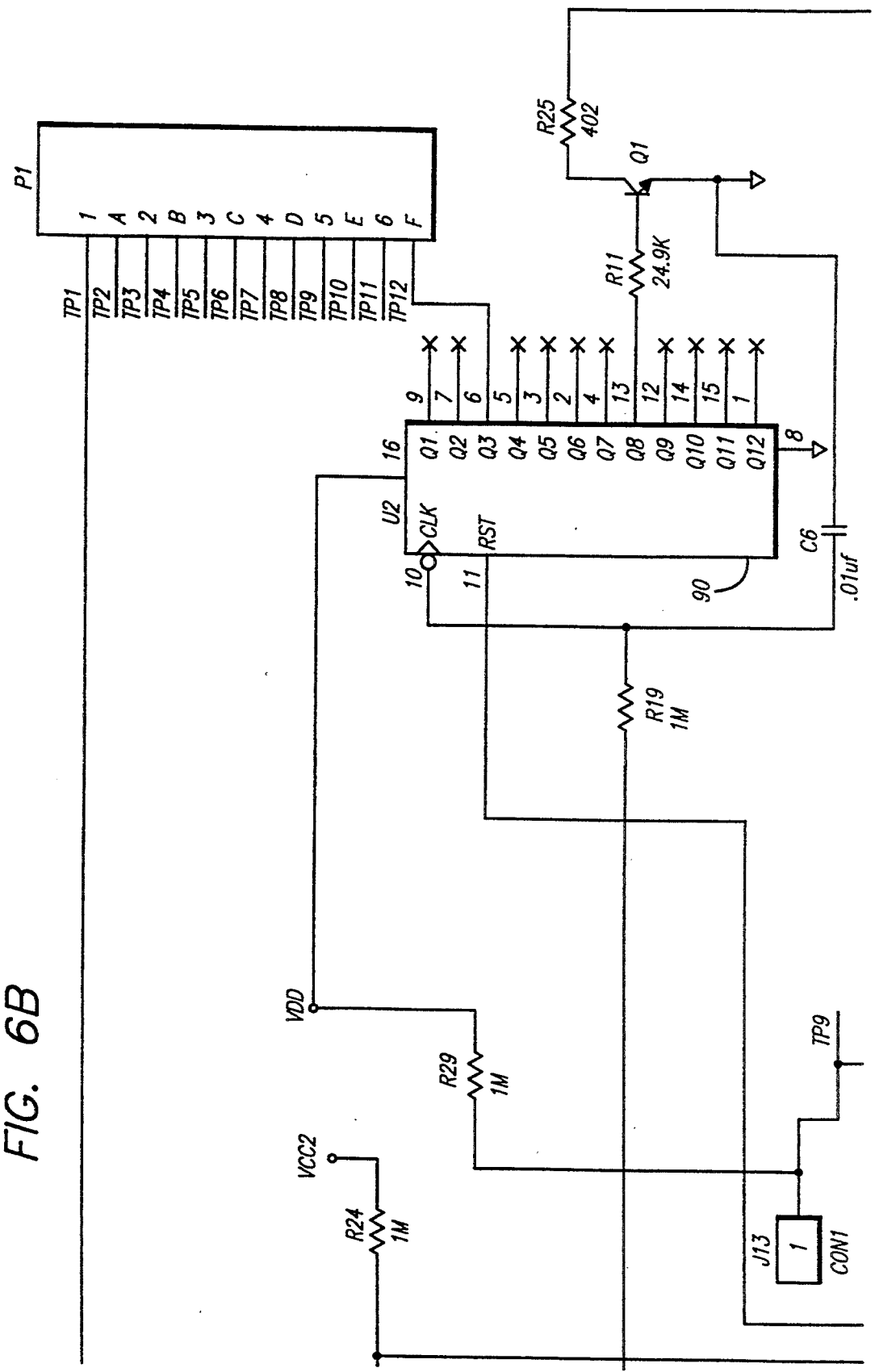
Figure 6C:
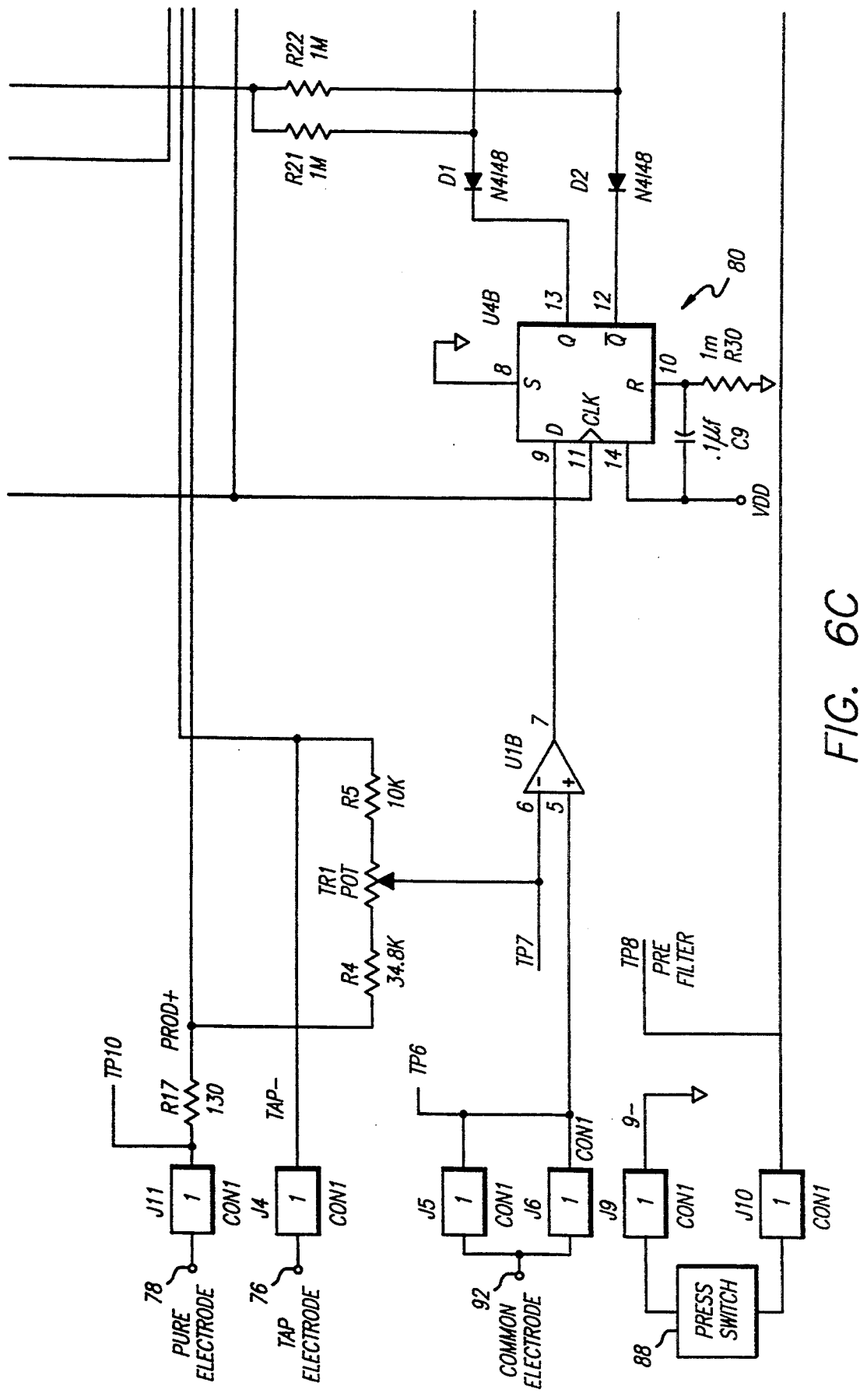
Figure 6D:
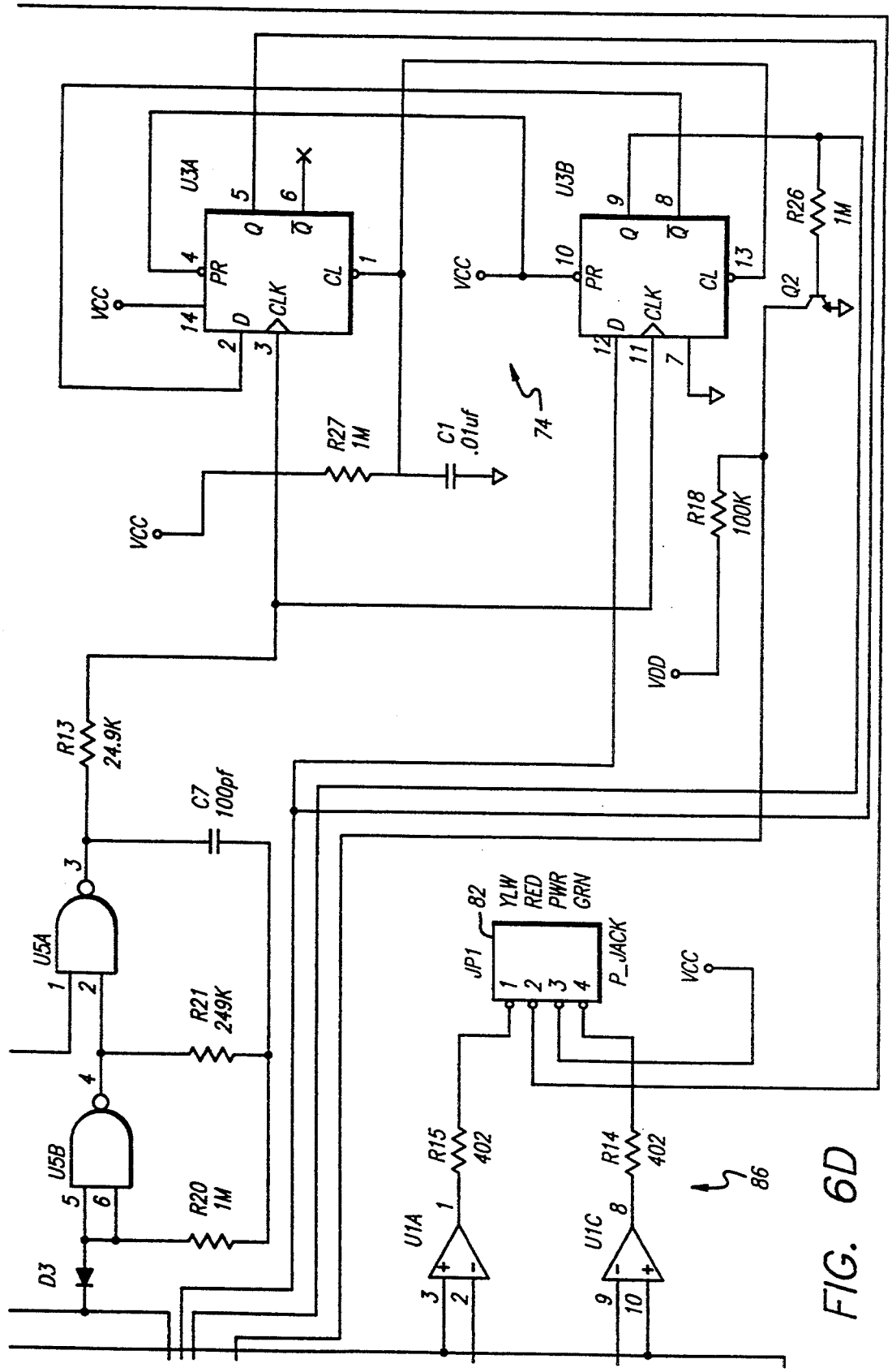

More specifically, initial movement of the inlet shut-off valve 42 from the closed position to a full open position as viewed in FIG. 3, displaces the magnet 64 on the shuttle piston 62 for resetting the reed switch 66 to a closed position. As shown in FIG. 6A, closure of the reed switch 66 connects the monitor circuit to the battery 70 to charge a capacitor C5 to a voltage level corresponding with battery voltage. The circuit is designed to charge the capacitor C5 over a time period sufficiently long so that mechanical rebound or bounce of the shut-off valve does not impact operation of the charging circuit 72.

Subsequently, when the reed switch 66 is opened during mid-cycle operation of the reverse osmosis unit 12, as described above, the charge stored by the capacitor C5 is discharged through a NAND gate U5C and a resistor R2, causing the output of the NAND gate U5C to be delivered as a pulse to the set pin of a flip-flop U4A. The set pulse functions to set the flip-flop U4A so that the "Q" output is high and the "not Q" output is low. The "not Q" low output biases a transistor Q3 to an "on" state, resulting in connection of the battery 70 to the input of a voltage regulator U6. This voltage regulator U6, as shown, regulates the voltage applied to the circuit components to a constant level of about 5-volts. The high output at the "Q" terminal of the flip-flop U4A turns a diode D3 to an "off" state, and thereby allows a clock U5B, U5A to switch to an "on" state. A counter U2 is also reset by the same "Q" high output of the flip-flop U4A.

The monitor circuit 74 that generates the test pulse for taking conductivity readings is comprised of flip-flops U3A, U3B, and the clock U5B, U5A. The "Q" output of flip-flop U3A is connected to the tap water electrode 76, and the "Q" output of flip-flop U3B is connected to the pure water electrode 78. An output capacitor C8 of the voltage regulator U6 charges, when the reed switch 66 is opened, in a short period of time, about 6 milliseconds before reaching the regulated voltage output. Accordingly, the flip-flops U3A, U3B that generate the test pulse applied to the electrodes are held in a reset condition for approximately 10 milliseconds, comprising the time for a capacitor C1 to charge to a voltage level insufficient to reset the flip-flops U3A, U3B. This short time delay also allows the clock U5B, U5A to turn on and stabilize. At the end of this short interval of about 10 milliseconds, the flip-flops U3A, U3B become active. The first clock cycle causes the "Q" output of the flip-flop U3A to go high while the "Q" output of the flip-flop U3B remains low, thereby making the pure water electrode 78 negative with respect to the tap water electrode 76. The second clock cycle causes the "Q" output of the flip-flop U3B to go high, such that the potential between the "Q" outputs of the two flip-flops U3A, U3B is zero. The third clock cycle causes the "Q" output of the flip-flop U3A to go low, thus making the pure water electrode 78 positive with respect to the negative tap water electrode 76. The fourth clock cycle causes the "Q" output of the flip-flop U3B to go low, making the potential between the electrodes 76, 78 zero.

The negative pulse through the electrodes 76, 78 on the first clock cycle is ignored with respect to taking a conductivity reading. When the pulse applied to the electrode 78 is positive, that pulse is also applied to a voltage divider circuit defined by resistors R4, R5 and an adjustable potentiometer TR1. The potentiometer TR1 is set to apply a proportional or comparative voltage to the negative terminal of a comparator U1B, the positive terminal of which is connected to a common electrode 92. When the comparison voltage representing the proportionate conductivity readings of the pure and tap water supplies exceed a reference point selected by adjustment of the potentiometer TR1, the output of the comparator will go high and indicate that pure water production is of unacceptable quality. Conversely, if the comparison voltage applied to the comparator U1B is less than the reference, the output of the comparator U1B is low and indicates that the condition of produced purified water is acceptable.

The test reading on the output side of comparator U1B is connected to the data input of a flip-flop U4B for the duration of the positive test pulse. When the test pulse terminates, the "Q" output of the flip-flop U3B switches to the low state, causing a transistor Q2 to turn "off", which in turn produces a positive clock edge pulse to be delivered to flip-flops U4A, U4B. As a result, the data is stored by the flip-flop U4B. Specifically, if the signal to the data input pin of the flip-flop U4B is low, indicating acceptable water quality, the state of the flip-flop U4B remains unchanged. However, if the data signal is high, indicating unacceptable water quality, the clock pulse changes the state of the flip-flop U4B so that its output "Q" is high and the output "not Q" is low.

The clock pulse referenced above is also supplied to the data input line of the flip-flop U4A. The clock pulse causes the "Q" output of the flip-flop U4A to go low and the "not Q" output to go high, thereby removing the bias from the transistor Q3 in order to switch that transistor Q3 to an "off" state. When the transistor Q3 turns "off" the voltage regulator U6 is disconnected from the battery 70 and the monitoring circuit is now in an "off" state.

When water is drawn from the system as by opening the faucet valve 18 to dispense water from the reservoir 16, the flow switch 84 connects the circuit to the battery 70, causing a capacitor C2 to charge. Instantaneously this applies battery voltage to the input of NAND gate U5D. While this voltage exceeds the threshold voltage of NAND gate U5D, the output of the NAND gate U5D goes low and biases the transistor Q3 to an "on" state. Accordingly, once again, the battery 70 is connected by the transistor Q3 to the voltage regulator U6, thereby turning on the voltage regulator and other circuit components.

A pair of voltage dividers including resistors R8, R23 and R9, R28 are connected to an amplifier U1D for biasing the display circuitry and also to provide an indication of a low battery voltage condition. In this regard, when the battery has an acceptable voltage level, the output of the amplifier U1D will be low to activate another voltage divider R10, R24. This voltage divider has a junction between R10 and R24 connected to comparators U1A and U1C, to create a reference voltage for the display circuitry. The other terminals of these two comparators are connected respectively to the "Q" and "not Q" outputs of the flip-flop U4B within which the test reading data has been stored, as previously described. When the stored data indicates acceptable water quality, the "Q" output of the flip-flop U4B is low and the "not Q" output of the flip-flop U4B is high. With this configuration, the yellow indicator light is disabled and the green indicator light is enabled to indicate visually the previously stored test reading, namely, that system operational performance is within acceptable limits. Conversely, when the nature of the signals on the outputs "Q" and "not Q" of the flip-flop U4B are reversed, indicating unacceptable water quality conditions, the green indicator light is disabled and the yellow indicator light is enabled, to indicate unacceptable system performance.

When the battery voltage decreases to an unacceptable low level, as determined by the voltage dividers R9, R28 and R8, R23, the output of the comparator U1D goes high. This output is connected to the comparators U1A and U1C, resulting effectively in disablement of the yellow and green lights to prevent illumination thereof, regardless of the stored test data, when the faucet valve is opened. Thus, when a test reading should normally be displayed, the absence of an illuminated light indicates that the battery needs to be replaced.

The pressure switch or sensor 88 on the prefilter stage 24, which may be located at the discharge port 46 of the prefilter stage 24, closes when the detected pressure indicates that the prefilter cartridge 30 needs to be replaced. The pressure switch connects the circuit common (ground) to the plus terminal of the comparators U1A and U1C, causing both comparators to have a low output and thereby enabling both of the yellow and green indicator lights when the faucet valve is open. When both lights are illuminated, the display thus indicates that the prefilter cartridge 30 should be replaced.

The counter 90 is provided as part of the circuitry to count the number of times that the flow switch 84 is closed upon opening of the faucet valve 18, without return movement of the reed switch 66 to a full open position at the conclusion of an off cycle. When the flow switch 84 is closed and the capacitor C2 charges, as described above, the NAND gate U5D produces a low output. As result, a capacitor C6 discharges through a resistor R19, such that a clock input of the counter 90 (U2) increments one count. The counter 90 increments each time the faucet valve is opened, but resets to zero when the reed switch 66 opens upon resumption of tap water flow following a system off cycle. In the preferred form, if the counter 90 increments to 128 prior to reset, a red indicator light is enabled to provide a visual indication that a system failure has occurred. In most cases, this failure is attributable to a mechanical failure of the inlet shut-off valve.

Figure 7:
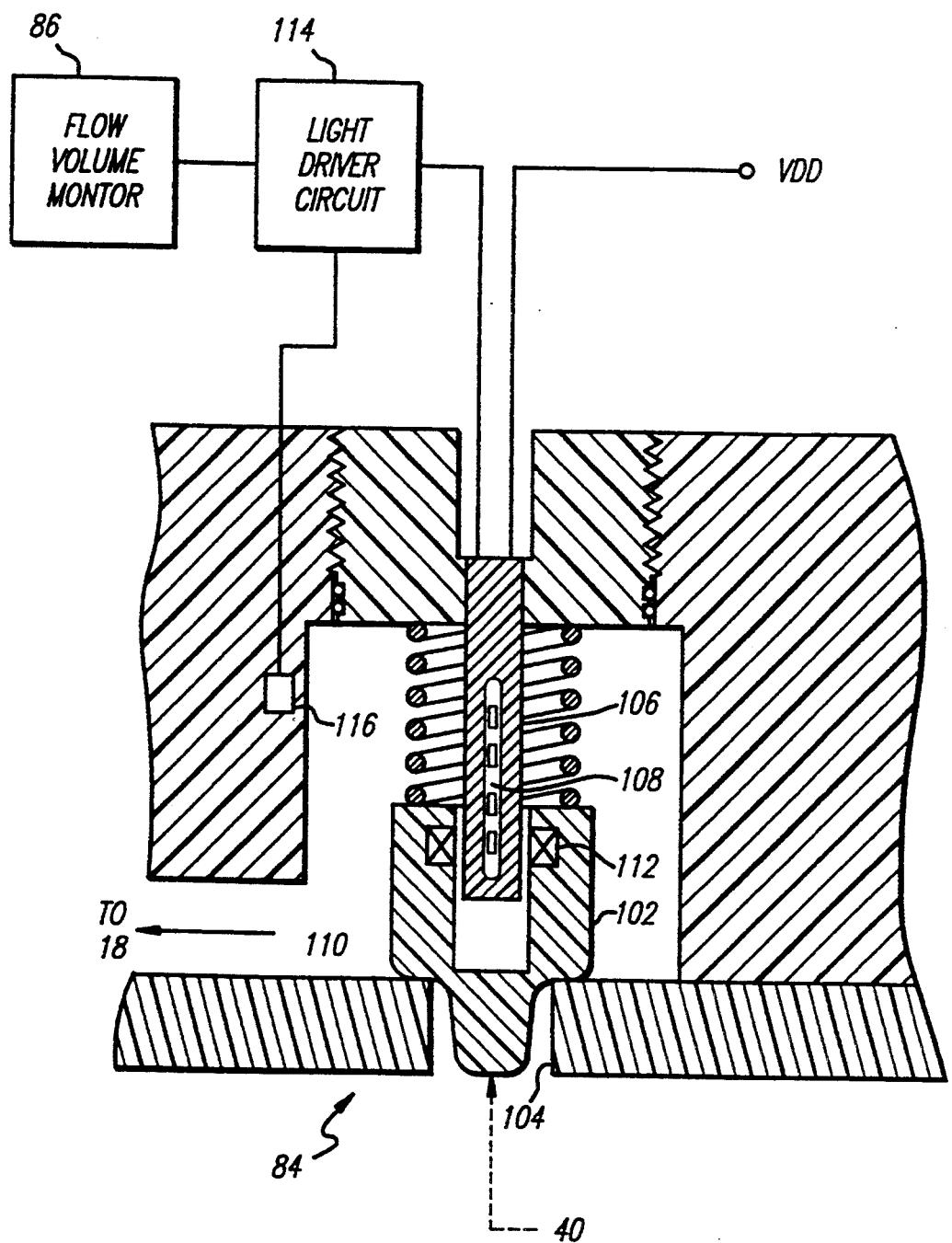
FIG. 7 is a fragmented sectional view, shown somewhat in schematic form, depicting an improved flow switch for use in the invention.

FIG. 7 shows one preferred form for the flow switch 84, installed along a dispense flow path leading from the dispense fitting 40 (FIGS. 1 and 2) to the faucet 18. The flow switch 84 includes a spring-loaded poppet 102 which moves to an open position relative to a flow port 104, when the faucet 18 or other dispense device is opened to initiate a dispense water flow. The degree of movement or displacement of the poppet 102 is a direct function of the volumetric flow rate through the dispense flow path.

The poppet 102 is slidably carried on a guide stem 106 having a reed switch 108 or the like fitted into a rear side counterbore 110 of the poppet. When the poppet 102 moves to an open position, a magnet 112 carried by the poppet is displaced over the reed switch 108 sufficiently to close the reed switch and supply power from the battery source to a flow volume monitor 114. The thus-energized monitor 114 then receives signals from a poppet position detector 116, such as a Hall effect transducer capable of tracking the poppet by monitoring the position of the magnet 112. Alternate poppet position sensors such as optical sensors may be used. In any case, the position sensor 116 signals the flow volume monitor 114 regarding poppet position when open so that a running accumulation of actual water volume dispensed can be derived. The flow volume monitor 114 can be appropriately coupled to the light driver circuit 86 as viewed in FIG. 7 to energize the indicator lights in a manner indicating that a predetermined volume of pure water has been appropriate signal to a solenoid-type valve actuator 142. The purification system thus resumes production of purified water, with the result that the reservoir water level eventually rises.

When the middle float 122 is moved upwardly on its stem 128, in response to rising reservoir water level reflective of a mid-cycle condition of operation, the float 122 opens the associated reed switch 138. This switch movement causes the reed circuit 140 to trigger and send the test pulse for taking a conductivity reading. As previously described, the test reading is stored in memory for later display. When the reservoir water level reaches the filled state, the upper float 120 rises to operate the associated reed switch, so that the actuator 142 will re-close the inlet shut-off valve 42.

Figure 10:
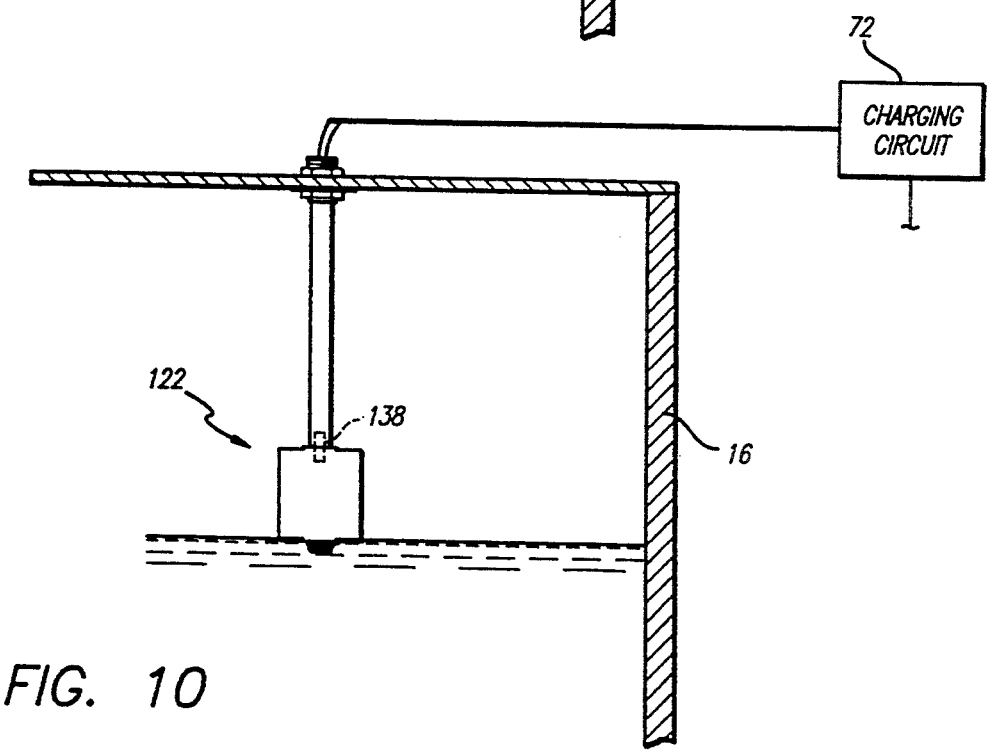
FIG. 10 is a schematic sectional view similar to FIG. 8, but illustrating a single float-mounted switch within the storage reservoir to control operation of the water quality monitor.

FIG. 10 shows another alternative embodiment, wherein a single float 122 is mounted within the reservoir for operating an associated reed switch 138 in a manner causing conductivity test readings to be taken at a mid-cycle condition of system operation. In this regard, the float 122 and reed switch 138 operate in the same manner as described with respect to FIGS. 8 and 9. However, in the embodiment of FIG. 10, operation of the inlet shut-off valve 42 may be responsive to differential pressure as previously shown and described with respect to FIGS. 2–4.

The invention thus provides an improved water monitoring circuit and system wherein all conductivity test readings are taken during a period of time when the reverse osmosis unit 12 is operating substantially at maximum performance level. By contrast, test readings are not taken during periods of operation at a performance level less than optimum, such as immediately after tap water flow is resumed to the system following an off cycle, or dispensed. When this occurs, it may be necessary or desirable to replace the filter cartridge 36 of the postfilter stage 28.

Figure 8:
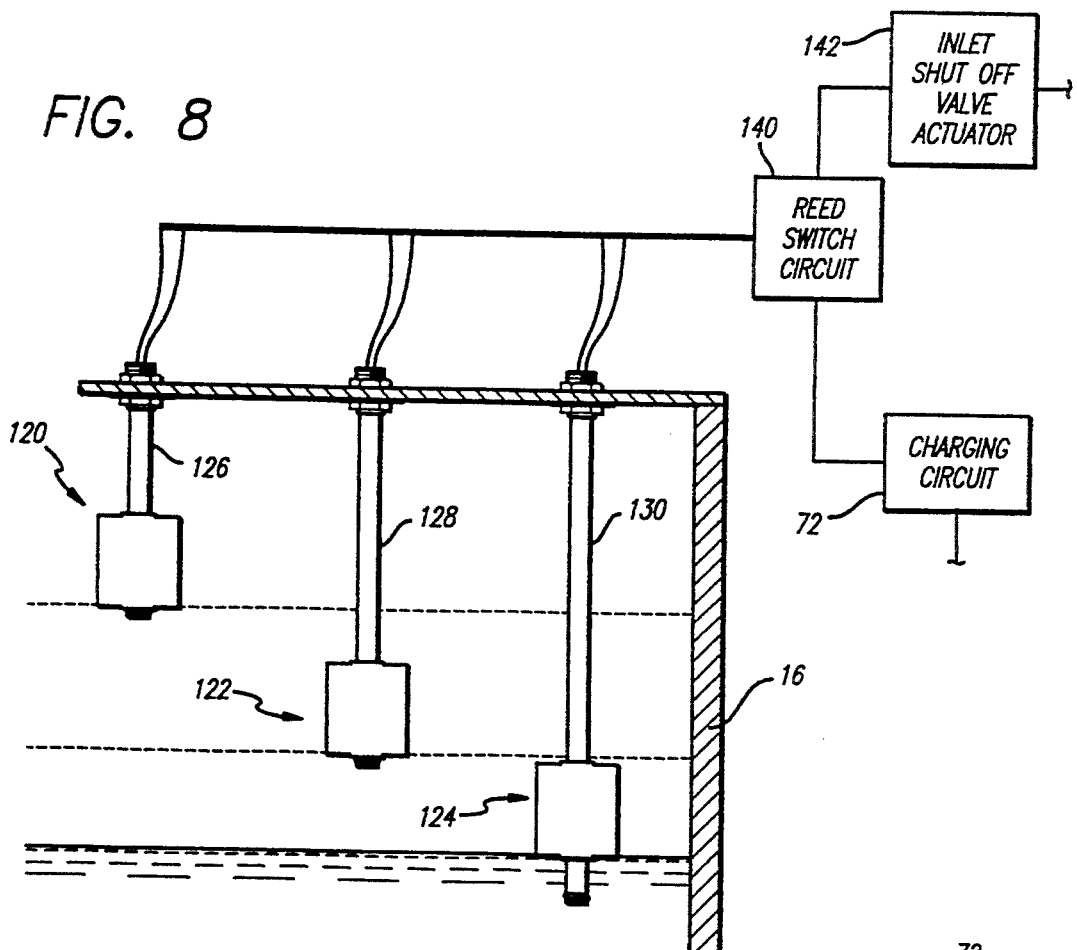
FIG. 8 is a fragmented and somewhat schematic sectional view illustrating one alternative preferred form of the invention wherein the water quality monitor is responsive to a plurality of float-mounted switches disposed within a pure water storage reservoir.
Figure 9:
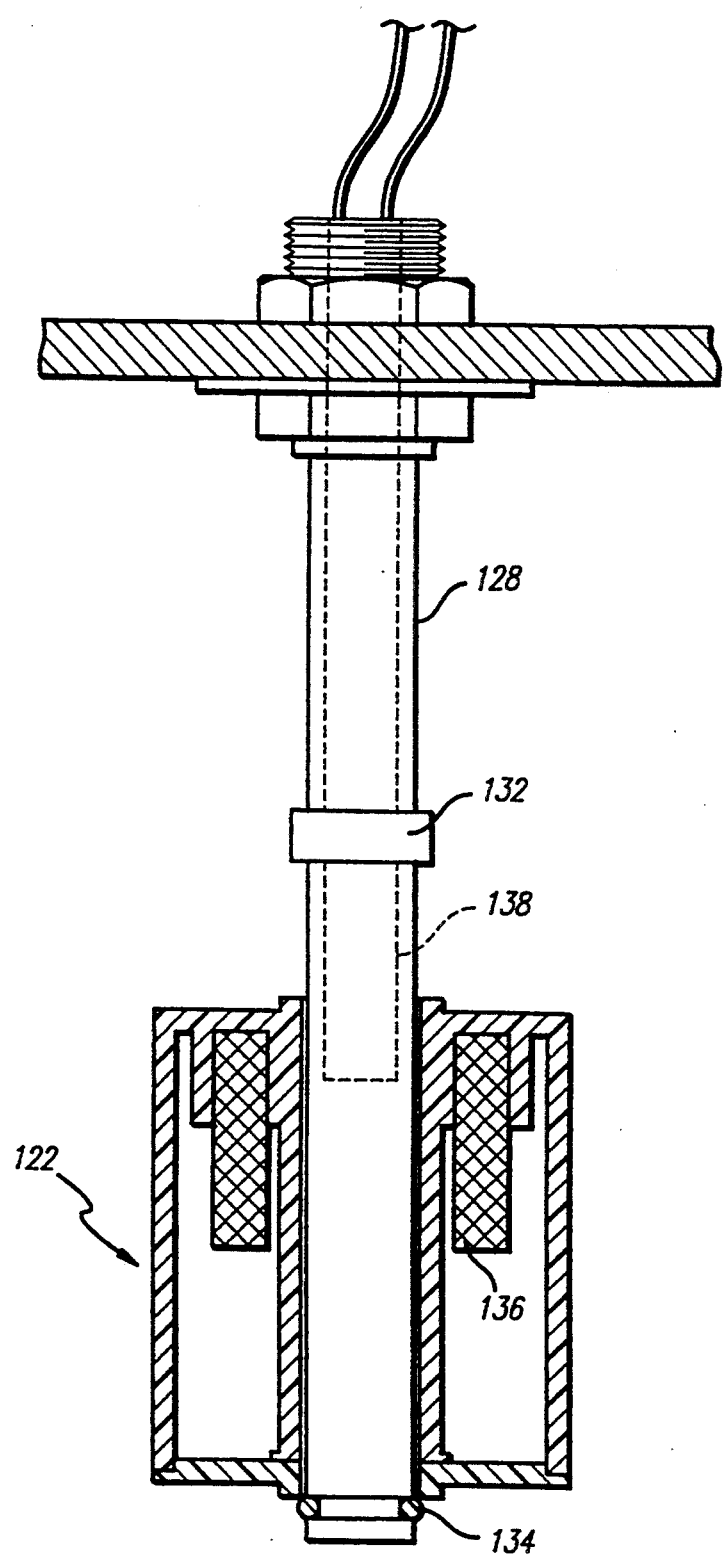
FIG. 9 is an enlarged fragmented vertical sectional view of one of the float-mounted switches of FIG. 8.

FIGS. 8 and 9 show one alternative preferred form of the invention, wherein operation of the purification system and the conductivity monitor are controlled by a plurality of float-mounted switches within the pure water storage reservoir 16. More particularly, as shown, three floats 120, 122 and 124 are mounted within the pure water chamber of the reservoir 16 for vertical displacement along vertically oriented mounting stems 126, 128 and 130 of different length. Each float is carried on its associated stem for back-and-forth movement within a limited vertical stroke between an upper shoulder 132 (FIG. 9) and a lower retaining ring 134. Each float also carries a magnet 136 for operating a reed switch 138 or the like carried on the associated stem, in response to rise and fall movement of the float. The three reed switches 138 are electrically connected to a reed switch circuit 140 (FIG. 8) which responds to the reservoir water level, as represented by movement of the floats 120, 122 and 124, to operate the inlet shut-off valve 42 and the conductivity monitor 20 (FIG. 1).

More specifically, when the reservoir 16 is in a substantially filled condition, dispensing of water from the reservoir causes the water level to fall. When the falling water level causes the middle float 122 to move to its lower position, the reed switch 138 associated with the float 122 is closed whereby the reed switch circuit 140 arms the charging circuit 72 so that a conductivity reading can subsequently be taken. When the water level falls sufficiently to cause the lower float 124 to move to its lower position, the reed switch 138 associated with the float 124 signals the circuit 140 to open the inlet shut-off valve 42, as by sending an immediately prior to closure of an inlet shut-off valve at the on set of an off cycle. Rather, the conductivity test readings are taken substantially during a mid-cycle operating condition. The reading is stored and subsequently displayed, in the preferred form, each time a faucet valve is opened to dispense water.

A variety of further modifications and improvements to the improved conductivity monitor of the present invention will be apparent to those skilled in the art. Accordingly, no limitation on the invention is intended by way of the foregoing description and accompanying drawings, except as set forth in the appended claims.

What is claimed is:

1. A water purification system, comprising:
    purification means for producing relatively purified water from a tap water supply;
    a reservoir for receiving and storing the purified water;
    dispensing means for dispensing the purified water from the system;
    inlet shut-off valve means responsive to the level of purified water within said reservoir and including a valve member movable to an open position permitting tap water flow to said purification means when the level of purified water within said reservoir is below a filled condition, and a closed position preventing tap water flow to said purification means when the level of purified water within said reservoir is at the filled condition; and a water quality monitor for testing the conductivity of the purified water and for providing an indication of unsatisfactory system performance when the conductivity indicates unsatisfactory system performance, said monitor including test means for taking a conductivity reading, means responsive to a rising water level and within said reservoir for actuating said test means to take a conductivity reading at a point in time substantially mid-cycle between movement of said valve member to said open position and subsequent movement of said valve member to said closed position, memory means for storing said conductivity reading, and indicator means for indicating said conductivity reading when said reading indicates unsatisfactory system performance.

2. The water purification system of claim 1 wherein said means within said reservoir for actuating said test means comprises float means for actuating said test means.

3. The water purification system of claim 2 wherein said float means includes switch means responsive to falling water level within said reservoir to reset said test means, said switch means being further responsive to rising water level within said reservoir to actuate said test means to take the conductivity reading.

4. The water purification system of claim 2 further including float means responsive to reservoir water level for moving said valve member between said open and closed positions when the reservoir water level is respectively at a predetermined minimum and maximum level.

5. The water purification system of claim 4 wherein said float means for actuating said test means is responsive to a reservoir water level generally mid-way between said predetermined minimum and maximum levels.

6. The water purification system of claim 1 wherein said purification means comprises a reverse osmosis unit.

7. The water purification system of claim 1 wherein said dispensing means comprises a faucet valve, and further wherein said indicator means is responsive to operation of said faucet valve to indicate the conductivity reading stored in said memory means.

8. The water purification system of claim 7 wherein said indicator means further includes means for indicating when said conductivity reading indicates unsatisfactory system performance.

9. The water purification system of claim 7 wherein said water quality monitor further includes counter means for counting the number of times the faucet valve is opened, and means for resetting said counter means each time said valve member moves toward the closed position, said indicator means including means for indicating when said counter means reaches a predetermined limit indicative of a system malfunction.

10. The water purification system of claim 1 wherein said indicator means further includes means for indicating when said conductivity reading indicates unsatisfactory system performance.

11. The water purification system of claim 1 wherein said water quality monitor includes a battery power supply, said indicator means including means for indicating when said battery power supply falls to a voltage level below a predetermined threshold.

12. The water purification system of claim 1 further including a prefilter stage having a replaceable prefilter cartridge for filtering tap water supplied to said purification means, said water quality monitor further including means for detecting the pressure drop across said prefilter cartridge, said indicator means including means for indicating when said pressure drop exceeds a predetermined limit.

13. The water purification system of claim 1 wherein said indicator means includes at least one indicator light.

14. The water purification system of claim 1 wherein said water quality monitor further includes flow volume monitor means for monitoring the volume of water dispensed by said dispensing means, said indicator means including means for indicating when a predetermined volume of water has been dispensed.

15. The water purification system of claim 14 further including a flow switch responsive to dispensing of water from the system to connect said flow volume monitor means to a source of electrical power.

16. In combination with a water purification system having purification means for producing relatively purified water from a tap water supply, a reservoir for receiving and storing the purified water, dispensing means for dispensing the purified water from the system, and an inlet shut-off valve movable between an open position permitting tap water inflow to the purification means when the purified water level within the reservoir is less than a filled condition, and a closed position preventing tap water inflow to the purification means when the purified water level within the reservoir is substantially at a filled condition, a water quality monitor, comprising:

a test circuit including at least one electrode in contact with the purified water for taking a conductivity reading representative of the relative purity of the purified water;

test circuit activation means responsive to operation of said purification means for activating said test circuit to take a conductivity reading at a point in time substantially mid-cycle between movement of said shut-off valve to the open position and subsequent movement of the shut-off valve to the closed position, said test circuit activation means including switch means for activating said test circuit, and a float means within said reservoir and responsive to a rising reservoir water level for operating said switch means;

memory means for storing said conductivity reading; and display means for displaying a visual signal representative of said conductivity reading.

17. A water quality monitor adapted for use with a water purification system having purification means for producing relatively purified water from a tap water supply, a reservoir for receiving and storing the purified water, dispensing means for dispensing the purified water from the system, and an inlet shut-off valve movable between an open position permitting tap water inflow to the purification means when the purified water level within the reservoir is at a predetermined minimum level less than a filled condition, and a closed position preventing tap water inflow to the purification means when the purified water level within the reservoir is substantially at a filled condition, said water quality monitor comprising:

a monitor circuit including a pure water electrode in contact with the purified water, said monitor circuit including means responsive to an activation signal to deliver a test pulse to said pure water electrode to take a conductivity reading representative of the quality of the purified water;

a charging circuit for generating and delivering said activation signal to said monitor circuit;

reset means for arming said charging circuit so that said charging circuit generates said activation signal, said reset means including float means mountable within said reservoir and responsive to a rising water level within said reservoir generally midway between said predetermined minimum level and said filled condition to cause said charging circuit to deliver said activation signal to said monitor circuit to take a conductivity reading;

memory means for receiving and storing an output signal from said monitor Circuit, said output signal representing the conductivity reading and thereby also representing the quality of the purified water; and display means for displaying a visual signal corresponding with said output signal stored by said memory means and thereby representing the quality of the purified water, said display means displaying said visual signal independently of the reservoir water level.

18. The water quality monitor of claim 17 wherein said dispensing means comprises a faucet valve, and further wherein said display means is responsive to operation of said faucet valve to indicate the conductivity reading represented by said output signal stored in said memory means.

19. The water quality monitor of claim 18 wherein said water quality monitor further includes counter means for counting the ,number of times the faucet valve is opened, and means for resetting said counter means each time said valve member moves toward the closed position, said display means including means for indicating when said counter means reaches a predetermined limit indicative of a system malfunction.

20. The water quality monitor of claim 17 wherein said water quality monitor includes a battery power supply, said display means including means for indicating when said battery power supply falls to a voltage level below a predetermined threshold.

21. The water quality monitor of claim 20 further including a prefilter stage having a replaceable prefilter cartridge for filtering tap water supplied to said purification means, said water quality monitor further including means for detecting the pressure drop across said prefilter cartridge, said display means including means for indicating when said pressure drop exceeds a predetermined limit.

* * * * *